(12) United States Patent
Hellberg

(10) Patent No.: US 11,684,925 B2
(45) Date of Patent: Jun. 27, 2023

(54) APPARATUS FOR HEATING TEST WATER

(71) Applicant: Thommy Hellberg, Helsinki (FI)

(72) Inventor: Thommy Hellberg, Helsinki (FI)

( * ) Notice: Subject to any disclaimer, the term of this patent is extended or adjusted under 35 U.S.C. 154(b) by 898 days.

(21) Appl. No.: 16/559,903

(22) Filed: Sep. 4, 2019

(65) Prior Publication Data
US 2020/0094257 A1 Mar. 26, 2020

(30) Foreign Application Priority Data

Sep. 4, 2018 (FI) .................................... 20180100

(51) Int. Cl.
*B01L 7/00* (2006.01)
*B65D 81/38* (2006.01)
*B01L 3/00* (2006.01)

(52) U.S. Cl.
CPC ............... *B01L 7/00* (2013.01); *B01L 3/502* (2013.01); *B65D 81/38* (2013.01)

(58) Field of Classification Search
None
See application file for complete search history.

(56) References Cited

U.S. PATENT DOCUMENTS

| | | | |
|---|---|---|---|
| 6,168,758 B1 | 1/2001 | Forsberg et al. | |
| 2005/0106750 A1* | 5/2005 | Tung | B01L 3/502 422/562 |
| 2006/0115873 A1* | 6/2006 | Peak | B01L 7/00 435/41 |
| 2010/0047125 A1 | 2/2010 | Ngoe Thu | |
| 2016/0097049 A1* | 4/2016 | Qian | C12Q 1/6806 422/534 |

FOREIGN PATENT DOCUMENTS

CN 207591899 U 7/2018

OTHER PUBLICATIONS

Finnish Patent Office, Search Report, U.S. Appl. No. 20/180,100, dated Apr. 2, 2019, 2 pages.
Thynell, T "The Finnish invention goes first to the world, and we have it in the spring: A quick test tells you in 10 minutes if there is a blue-green algae in the water" published Jan. 15, 2018, https://yle.fi/uutiset/3-10022891, 1 page (English Translation).

* cited by examiner

*Primary Examiner* — Matthew D Krcha
(74) *Attorney, Agent, or Firm* — Ziegler IP Law Group, LLC

(57) ABSTRACT

An apparatus for heating test water includes a test container for receiving the test water, and a heating container for installation of the test container. The heating container contains burnt lime that heats the test water when being mixed with water to be tested arranged in the heating container.

3 Claims, 3 Drawing Sheets

APPARATUS FOR HEATING TEST WATER

FIELD

The aspects of the disclosed embodiments relate to an apparatus for heating test water, comprising a test container for receiving the test water, and a heating container for installation of the test container therein, the heating container containing burnt lime that heats the test water when being mixed with water to be tested arranged in the heating container. The apparatus is used for heating the test water in order to disrupt the cells of blue-green algae for testing purposes.

BACKGROUND

An apparatus known per se is formed by a heating container, wherein a test container and a cap are screwed by means of threads onto the heating container. The top surface of the cap is provided with holes through which water is able to flow into the heating container and mixes with lime. As the water is boiling, all pressure is directed upwards, generating hot vapour that may burn, and causing the mixing of primary water and secondary water, which raises the pH of the test water.

SUMMARY

The aspects of the disclosed embodiments are directed to remedy the defects mentioned above. In the apparatus according to the disclosed embodiments a cap of a heating container comprises a top flange to which a test container is fitted such that the test container is open from the top and test water is able to flow in when the apparatus is submerged in water to be tested, and a downwardly pointing cylindrical protrusion of the cap fastens to the outer perimeter of the heating container by means of lugs such that a gap is left between the protrusion of the cap and the heating container such that water to be tested may flow into the heating container through the gap when the apparatus is submerged in the water to be tested.

In one embodiment of the invention the outer perimeter of the heating container is provided with a surrounding flange to which the lugs, for example four lugs, attach when the cap is pressed onto the heating container. A snap-type connection may thus be formed between the heating container and the cap.

The form of the cap according to the invention has now been modified such that the cap is not screwed in position but is placed in position onto the flange of the surface of the heating container so as to "float" on four lugs. As the water is boiling, most of the pressure is directed downwards along the side of the heating container.

When a gap is left between the protrusion of the cap and the heating container, the handling of the apparatus may be facilitated as the cap stays cooler during use of the apparatus.

DESCRIPTION OF THE DRAWINGS

The invention is described below by way of examples with reference to the accompanying drawings, in which.

DETAILED DESCRIPTION OF THE DISCLOSED EMBODIMENTS

Figure 1:
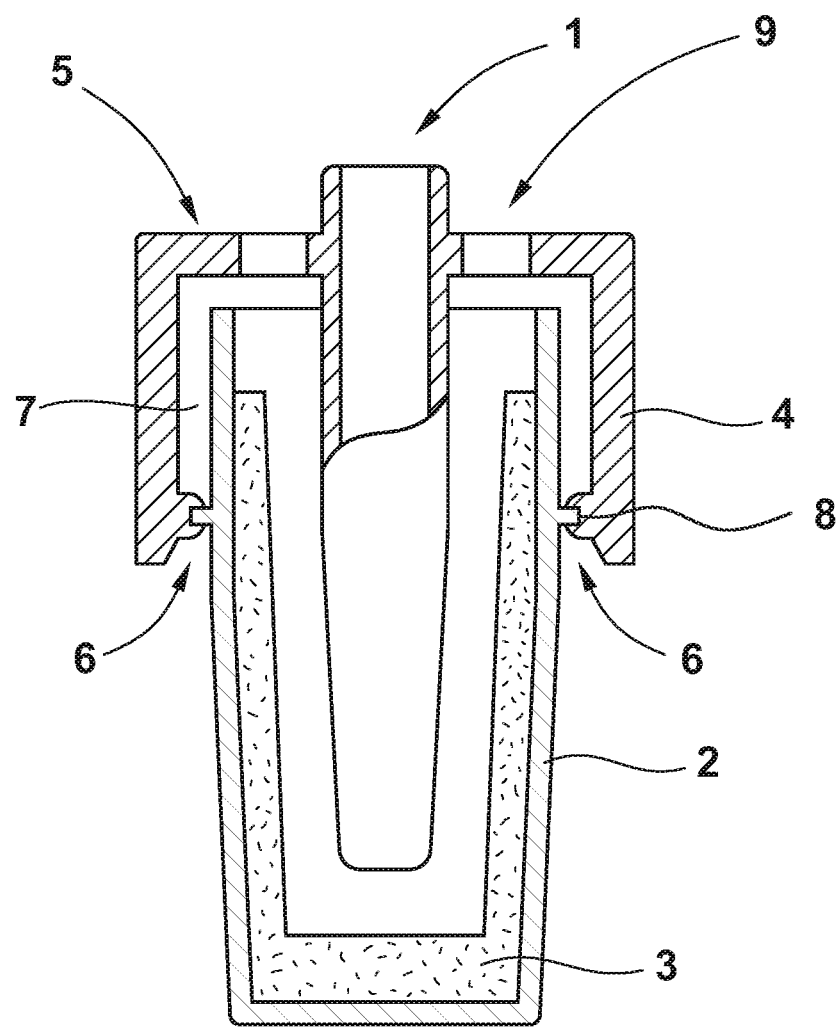
FIG. 1 is a sectional view of an apparatus for heating test water.

With reference to drawing FIG. 1, the apparatus comprises a test container 1 for receiving test water, i.e. primary water, and a heating container 2 for installation of the test container therein, the heating container containing burnt lime 3 that heats the test water when being mixed with water to be tested arranged in the heating container. The waters are obtained from the same water source location. A cap of the heating container 2 comprises a top flange 5 to which the test container 1 is fitted such that the test container 1 is open from the top and the test water is able to flow in when the apparatus is submerged in the water to be tested. A downwardly pointing cylindrical protrusion 4 of the cap fastens to the outer perimeter of the heating container 2 by means of lugs 6 such that a gap 7 is left between the downwardly pointing cylindrical protrusion 4 of the cap and the heating container 2 such that water to be tested may flow into the heating container 2 through the gap when the apparatus is submerged in the water to be tested. Water is also let into the heating container through holes 9 of the flange 5. The outer perimeter of the heating container 2 is provided with a surrounding flange 8 to which the lugs 6, for example four lugs, attach when the cap is pressed onto the heating container 2.

Figure 2:
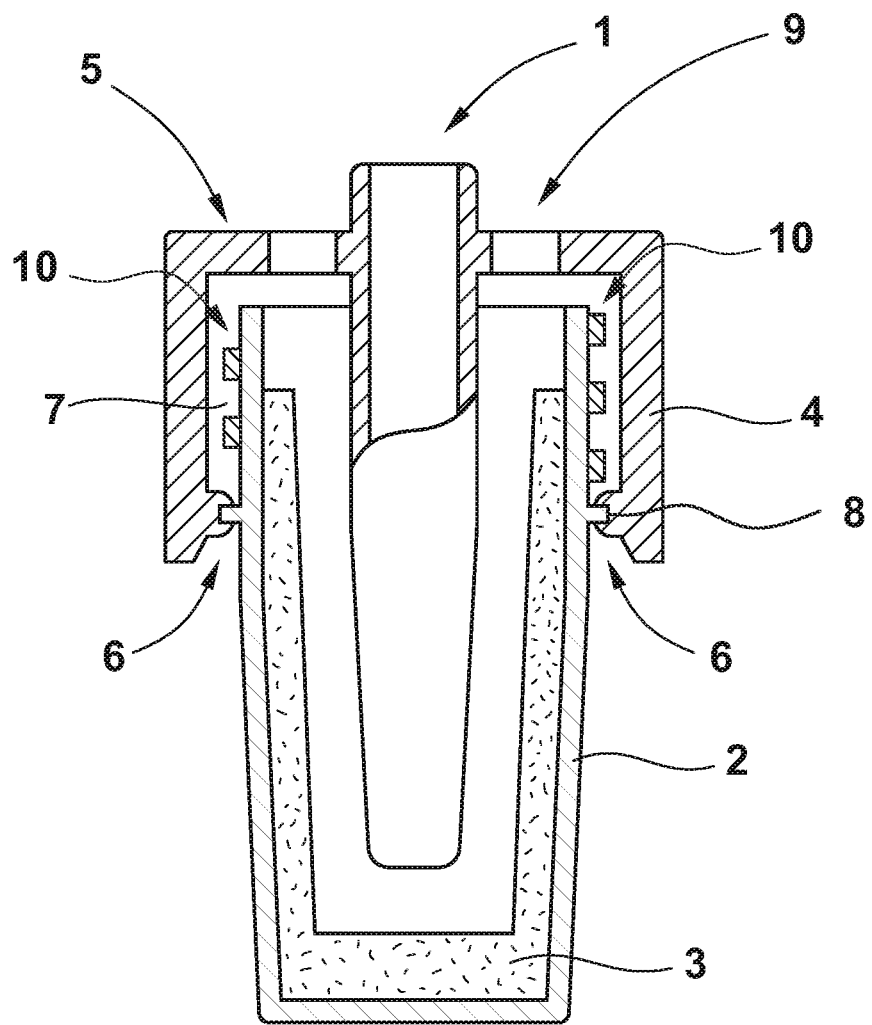
FIG. 2 is a sectional view of another apparatus for heating test water.

Drawing FIG. 2 illustrates an apparatus for heating test water that differs from the embodiment of FIG. 1 in that in the apparatus of FIG. 2, in the upper part of the heating container 2 there are threads 10 above the flange 8, whereby the container may work for different liquid samples when the container is closed with a regular screw cap.

Figure 3:
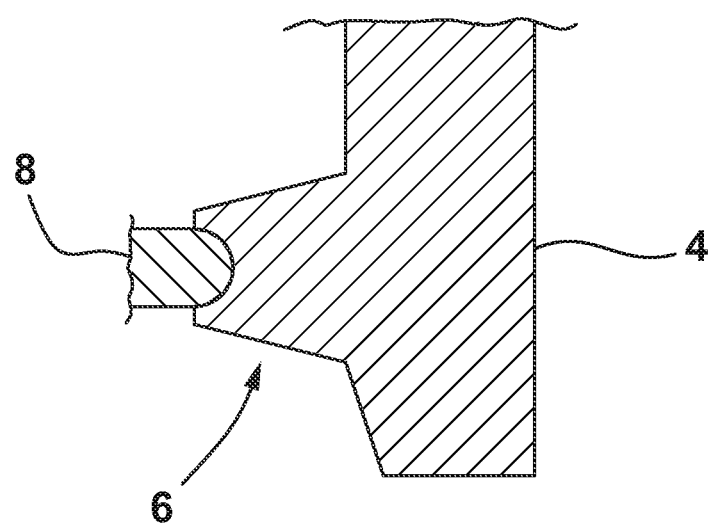
FIG. 3 illustrates structural details from an apparatus for heating test water.

Drawing FIG. 3 illustrates a partial cross-section of an apparatus for heating test water that may be substantially similar to the embodiment of FIG. 1 or to the embodiment of FIG. 2. FIG. 3 shows part of the flange 8 to which the lug 6 attaches.

In some embodiments the cylindrical protrusion of the cap may have a centre axis, and the diameter of the cap in a direction perpendicular to the centre axis may be for example 1 cm-4 cm or 2 cm-3 cm.

In some embodiments the cylindrical protrusion of the cap may have a centre axis, and the height of the apparatus in the direction of the centre axis may be for example 4 cm-9 cm or 5 cm-8 cm or 6 cm-7 cm.

In some embodiments the width of the gap may be for example 0.5 mm-5 mm, or 1 mm-4 mm or 2 mm-3 mm.

The invention claimed is:

1. An apparatus for heating test water comprising:
a test container for receiving the test water, and
a heating container for installation of the test container therein, the heating container containing burnt lime that heats the test water when being mixed with water to be tested arranged in the heating container,
wherein a cap of the heating container comprises a top flange to which the test container is fitted such that the test container is open from the top and the test water flows in when the apparatus is submerged in the water to be tested, and
a downwardly pointing cylindrical protrusion of the cap fastens to the outer perimeter of the heating container with lugs, and a gap is left between the protrusion of the cap and the heating container when the cap is fully fastened to the outer perimeter of the heating container such that the water to be tested flows into the heating container through the gap when the apparatus is submerged in the water to be tested.

2. The apparatus according to claim 1, wherein the outer perimeter of the heating container is provided with a surrounding flange to which the lugs attach when the cap is pressed onto the heating container.

3. The apparatus according to claim 2, wherein, in the upper part of the heating container, threads are arranged above the flange.

* * * * *